US00PP22382P2

(12) United States Plant Patent
Dümmen

(10) Patent No.: US PP22,382 P2
(45) Date of Patent: Dec. 20, 2011

(54) ***BEGONIA* PLANT NAMED 'BBDRAWHIBLU'**

(50) Latin Name: *Begonia×hiemalis*
Varietal Denomination: BBDRAWHIBLU

(75) Inventor: Tobias Gunter Dümmen, Rheinberg (DE)

(73) Assignee: Begonia Breeders Association B.V., Rijsenhout (NL)

( * ) Notice: Subject to any disclaimer, the term of this patent is extended or adjusted under 35 U.S.C. 154(b) by 0 days.

(21) Appl. No.: 12/807,246

(22) Filed: Aug. 31, 2010

(51) Int. Cl.
*A01H 5/00* (2006.01)

(52) U.S. Cl. ..... Plt./344

(58) Field of Classification Search ..... Plt./348
See application file for complete search history.

(56) References Cited

U.S. PATENT DOCUMENTS

PP19,700 P2 * 2/2009 Dummen ..... Plt./343

* cited by examiner

*Primary Examiner* — Wendy C Haas
(74) *Attorney, Agent, or Firm* — C. A. Whealy

(57) ABSTRACT

A new and distinct cultivar of *Begonia* plant named 'BBDRAWHIBLU', characterized by its upright and mounded plant habit; freely branching habit; numerous double flowers that are white and pink in color; and good postproduction longevity.

1 Drawing Sheet

Botanical designation: *Begonia×hiemalis.*
Cultivar denomination: 'BBDRAWHIBLU'.

CROSS-REFERENCED TO CLOSELY-RELATED APPLICATIONS

Title: *Begonia* Plant Named 'BBDRASOPI'
(U.S. Plant patent application Ser. No. 12/807,247)
Title: *Begonia* Plant Named 'BBDRASUN'
(U.S. Plant patent application Ser. No. 12/807,248)

BACKGROUND OF THE INVENTION

The present invention relates to a new and distinct cultivar of *Begonia* plant, botanically known as *Begonia×hiemalis*, commercially known as Elatior *Begonia*, and hereinafter referred to by the name 'BBDRAWHIBLU'.

The new *Begonia* plant is a naturally-occurring whole plant mutation of the *Begonia×hiemalis* cultivar BBDRA, disclosed in U.S. Plant Pat. No. 19,700. The new *Begonia* was discovered and selected by the Inventor from within a population of plants of 'BBDRA' in a controlled greenhouse environment in Rijsenhout, The Netherlands during the spring of 2007.

Asexual reproduction of the new *Begonia* plant by terminal cuttings in a controlled greenhouse environment in Rijsenhout, the Netherlands since the autumn of 2007, has shown that the unique features of this new *Begonia* plant are stable and reproduced true to type in successive generations.

SUMMARY OF THE INVENTION

Plants of the new *Begonia* have not been observed under all possible environmental conditions. The phenotype may vary somewhat with variations in cultural practices and environment conditions such as temperature and light intensity, without, however, any variance in genotype.

The following traits have been repeatedly observed and are determined to be the unique characteristics of 'BBDRAWHIBLU'. These characteristics in combination distinguish 'BBDRAWHIBLU' as a new and distinct *Begonia* plant:

1. Upright and mounded plant habit.
2. Freely branching habit.
3. Numerous double flowers that are white and pink in color.
4. Good postproduction longevity.

Plants of the new *Begonia* differ primarily from plants of the parent, 'BBDRA', primarily in flower color as plants of 'BBDRA' have light red-colored flowers. In addition, flower of plants of 'BBDRA' appear to be more "filled" than flowers of the new *Begonia.*

Plants of the new *Begonia* differ primarily from plants of *Begonia×hiemalis* 'BBDRASOPI', disclosed in U.S. Plant patent application Ser. No. 12/007,247, and plants of *Begonia×hiemalis* 'BBDRASUN', disclosed in U.S. Plant patent application Ser. No. 12/007,248, in flower color as plants of 'BBDRASOPI' and pink-colored flowers and plants of 'BBDRASUN' have yellow and pink-colored flowers.

Plants of the new *Begonia* can be compared to plants of *Begonia×hiemalis* 'BBTAM', disclosed in U.S. Plant Pat. No. 19,800. In side-by-side comparisons conducted in Rijsenhout, The Netherlands, plants of the new *Begonia* differed from plants of 'BBTAM' primarily in flower color as plants of 'BBTAM' had salmon pink-colored flowers.

BRIEF DESCRIPTION OF THE PHOTOGRAPH

The accompanying colored photograph illustrates the overall appearance of the new *Begonia* plant showing the colors as true as it is reasonably possible to obtain in colored reproductions of this type. Colors in the photograph may differ slightly from the color values cited in the detailed botanical description which accurately describe the colors of the new *Begonia* plant. The photograph comprises a side perspective view of a typical flowering plant of 'BBDRAWHIBLU' grown in a container.

DETAILED BOTANICAL DESCRIPTION

Plants used for the aforementioned photograph and following observations and measurements were grown during the spring and summer in 13-cm containers in a shaded glass-covered greenhouse in Rijsenhout, The Netherlands and grown under typical *Begonia* production practices. During the production of the plants day and night temperatures ranged from 15° C. to 20° C. and maximum light levels were 18,000 lux. Plants were twelve weeks old when the photograph and description were taken. In the following description, color references are made to The Royal Horticultural Society Colour Chart, 2001 Edition, except where general terms of ordinary dictionary significance are used.

Botanical classification: *Begonia×hiemalis* 'BBDRAWHIBLU'.

Commercial classification: Elatior *Begonia*.

Parentage: Naturally-occurring whole plant mutation of *Begonia×hiemalis* 'BBDRA', disclosed in U.S. Plant Pat. No. 19,700.

Propagation:

*Type.*—By terminal vegetative cuttings.

*Time to initiate roots.*—About 14 days at temperatures of 20° C.

*Time to produce a rooted young plant.*—About 20 to 35 days at temperatures of 20° C.

*Root description.*—Medium in thickness, fibrous, white in color; plants of the new *Begonia* have not been observed to form tubers.

*Rooting habit.*—Freely branching; moderately dense.

Plant description:

*Plant form.*—Compact, upright and mounded plant habit, inverted triangle; freely branching with good stem and stem base strength; flowers are fully double and abundant; moderately vigorous growth habit.

*Plant height.*—About 20 cm to 25 cm.

*Plant width.*—About 25 cm to 30 cm.

*Basal branch description.*—Quantity: Freely basal branching with about five to six basal branches developing per plant. Length: About 9 cm to 13 cm. Diameter: About 1 cm to 3 cm. Texture: Smooth, glabrous. Color: Close to 138B.

*Leaf description.*—Arrangement: Simple, alternate. Length: About 8 cm to 9 cm. Width: About 5 cm to 6 cm. Shape: Roughly deltoid. Apex: Broadly obtuse. Base: Cordate to oblique. Margin: Senate. Texture, upper and lower surfaces: Smooth, glabrous. Venation pattern: Palmate. Color: Developing leaves, upper surface: Close to 131A. Developing leaves, lower surface: Close to 139A. Fully expanded leaves, upper and lower surfaces: Close to 131C, venation, close to 131C. Petiole length: About 4 cm to 6 cm. Petiole diameter: About 4 mm. Petiole texture, upper and lower surfaces: Smooth, glabrous. Petiole color, upper and lower surfaces: Close to 131C.

Flower description:

*Flowering habit.*—Double flowers with numerous tepals arranged in axillary cymes; typically five to six open flowers per cyme; many cymes in flower simultaneously; flowers positioned upright and outwardly above the foliar plane.

*Fragrance.*—Not detected.

*Natural flowering season.*—Plants will flower continuously year round in the greenhouse, however plants flower earlier and more abundantly during the summer in The Netherlands.

*Postproduction longevity.*—Good postproduction longevity, flowers last about four weeks on the plant; flowers persistent.

*Cyme height.*—About 6 cm to 8 cm.

*Cyme diameter.*—About 6 cm to 7 cm.

*Flowers.*—Shape: Oval; rose-like. Diameter: About 4 cm to 5 cm. Depth: About 1 cm.

*Flower buds.*—Shape: Ovate. Length: About 1 cm to 1.5 cm. Diameter: About 2 cm. Color: Close to 52D.

*Tepals.*—Arrangement: Rosette. Quantity: About 10 to 15 per flower. Length: About 2 cm to 3 cm. Width: About 3 cm to 4 cm. Shape: Obovate to rounded. Apex: Rounded, obtuse. Base: Cordate. Margin: Entire to emarginate. Texture, upper and lower surfaces: Smooth, glabrous; satiny. Color: When opening and fully opened, upper surface: Center tepals, close to 155D; outer tepals, close to 52D. When opening and fully opened, lower surface: Center tepals, close to 155D; outer tepals, close to 52D.

*Flower bracts.*—Quantity/arrangement: Two, opposite. Shape: Broadly ovate. Apex: Obtuse. Margin: Entire. Texture, upper and lower surfaces: Smooth, glabrous. Color, upper surface: Close to 144D and at the margins, close to 45C. Color, lower surface: Close to 145B and at the margins, close to 45C.

*Peduncles.*—Angle: Erect to about 30° to 45° from vertical. Length: About 4 cm to 5 cm. Diameter: About 3 mm to 4 mm. Strength: Strong. Texture: Smooth, glabrous. Color: Close to 144B.

*Pedicels.*—Angle: About 30° to 45° from the peduncle. Length: About 2 cm to 3 cm. Diameter: About 2 mm to 3 mm. Strength: Strong. Texture: Smooth, glabrous. Color: Reddish green.

*Reproductive organs.*—Stamens: None observed. Pistils: None observed.

*Seed/fruit.*—Seed and fruit production have not been observed.

Disease/pest resistance: Resistance to pathogens and pests common to *Begonia* has not been observed.

Temperature tolerance: Plants of the new *Begonia* have been observed to tolerate temperatures from about 10° C. to about 35° C.

It is claimed:

1. A new and distinct *Begonia* plant named 'BBDRAWHIBLU' as illustrated and described.

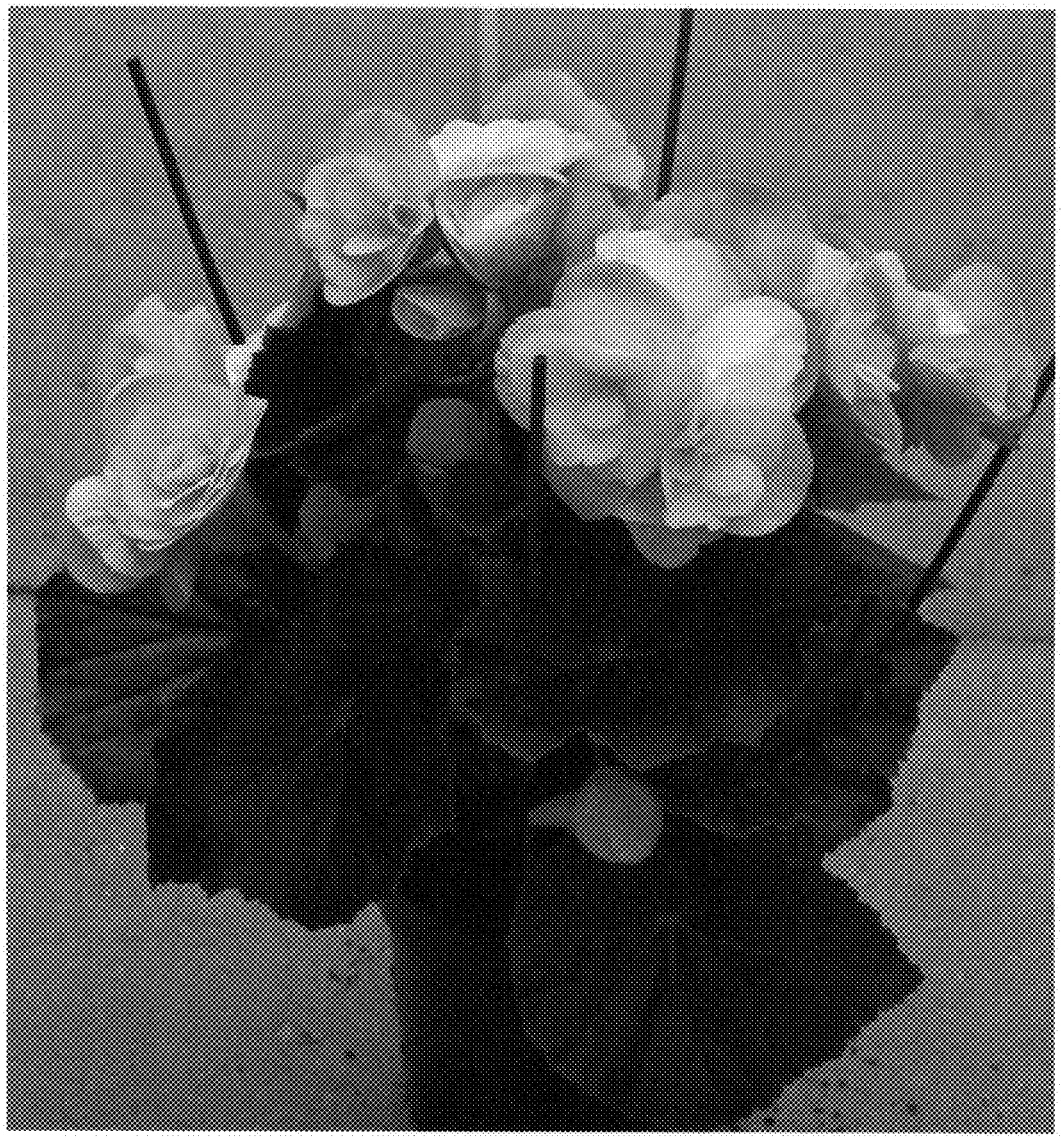

* * * * *